(12) United States Patent
Hoffmann

(10) Patent No.: US 12,179,197 B2
(45) Date of Patent: Dec. 31, 2024

(54) MICROFLUIDIC SEQUENCING DEVICE FOR MULTIPLYING AND SEPARATING MOLECULAR CHAINS, AND METHOD FOR SEPARATING MOLECULAR CHAINS OBTAINED FROM AN AMPLIFICATION REACTION

(71) Applicant: Robert Bosch GmbH, Stuttgart (DE)

(72) Inventor: Jochen Hoffmann, Renningen (DE)

(73) Assignee: Robert Bosch GmbH, Stuttgart (DE)

( * ) Notice: Subject to any disclaimer, the term of this patent is extended or adjusted under 35 U.S.C. 154(b) by 1088 days.

(21) Appl. No.: 17/051,688

(22) PCT Filed: May 2, 2019

(86) PCT No.: PCT/EP2019/061255
§ 371 (c)(1),
(2) Date: Oct. 29, 2020

(87) PCT Pub. No.: WO2019/215010
PCT Pub. Date: Nov. 14, 2019

(65) Prior Publication Data
US 2021/0237063 A1 Aug. 5, 2021

(30) Foreign Application Priority Data

May 8, 2018 (DE) ...................... 10 2018 207 106.3

(51) Int. Cl.
*C12Q 1/6869* (2018.01)
*B01L 3/00* (2006.01)

(52) U.S. Cl.
CPC ... *B01L 3/502753* (2013.01); *B01L 3/502707* (2013.01); *B01L 2300/0681* (2013.01); *B01L 2400/0424* (2013.01); *C12Q 1/6869* (2013.01)

(58) Field of Classification Search
CPC ......... B01L 3/502753; B01L 3/502707; B01L 2300/0681; B01L 2400/0424; C12Q 1/6869
See application file for complete search history.

(56) References Cited

U.S. PATENT DOCUMENTS

| | | |
|---|---|---|
| 6,406,893 B1 | 6/2002 | Knapp et al. |
| 2002/0175079 A1 | 11/2002 | Christel et al. |

(Continued)

FOREIGN PATENT DOCUMENTS

| | | |
|---|---|---|
| WO | 2014/024041 A1 | 2/2014 |
| WO | 2016/154337 A2 | 9/2016 |

OTHER PUBLICATIONS

International Search Report corresponding to PCT Application No. PCT/EP2019/061255, mailed Aug. 9, 2019 (German and English language document) (6 pages).

*Primary Examiner* — Brian J. Sines
(74) *Attorney, Agent, or Firm* — Maginot, Moore & Beck LLP

(57) ABSTRACT

A microfluidic sequencing device for multiplying and separating molecular chains, and which is designed to receive biochemical material, includes at least one supply opening for supplying biochemical material into the sequencing device. The sequencing device additionally has at least one microfluidic separation unit, which has at least one separation channel with at least one amplification cavity for multiplying molecular chains supplied via the supply opening as the biochemical material and with at least one separating unit which is connected or can be connected to the amplification cavity microfluidically and includes a multi-porous material. The separating unit is designed to separate nucleic acids from other macromolecular components and/or to separate nucleic acids. Furthermore, the sequencing device has at least one discharge opening for (Continued)

discharging nucleic acids separated in the separation unit as biochemical material out of the sequencing device.

16 Claims, 5 Drawing Sheets

(56) References Cited

U.S. PATENT DOCUMENTS

| | | |
|---|---|---|
| 2013/0004956 A1 | 1/2013 | Landers et al. |
| 2013/0217026 A1 | 8/2013 | Egan et al. |
| 2014/0179909 A1 | 6/2014 | O'Halloran et al. |
| 2014/0248711 A1* | 9/2014 | Monbouquette ............................ G01N 33/48721 436/501 |

* cited by examiner

MICROFLUIDIC SEQUENCING DEVICE FOR MULTIPLYING AND SEPARATING MOLECULAR CHAINS, AND METHOD FOR SEPARATING MOLECULAR CHAINS OBTAINED FROM AN AMPLIFICATION REACTION

This application is a 35 U.S.C. § 371 National Stage Application of PCT/EP2019/061255, filed on May 2, 2019, which claims the benefit of priority to Serial No. DE 10 2018 207 106.3, filed on May 8, 2018 in Germany, the disclosures of which are incorporated herein by reference in their entirety.

BACKGROUND

The disclosure proceeds from a sequencing device or a method. A computer program is also subject matter of the present disclosure.

Deciphering the genetic code, also called DNA sequencing, is a standard method in research and medicine. The established dideoxy sequencing method by Frederick Sanger involves the use of modified nucleotides in an amplification reaction, i.e., a polymerase chain reaction (PCR). If they are incorporated into a resultant PCR product strand by a polymerase, it is no longer possible for a further nucleotide to be incorporated and the product strand remains in the particular length. Thereafter, the product fragments are resolved by gel electrophoresis. The distribution of lengths of the product fragments terminated with a certain nucleobase makes it possible to determine the sequence of the PCR product unambiguously. In the case of next-generation sequencing (NGS) methods by contrast, sequencing-by-synthesis methods are mainly used. The DNA molecules to be sequenced are first clonally amplified and bound on a solid phase. During the synthesis of the product strand, the incorporation of individual fluorescently labeled nucleotides is measured, this ultimately making it possible to deduce the sequence. Recently, single-molecule sequencers have come onto the market. Compared to NGS, these systems omit the clonal amplification of nucleic acids, and as a result, sequencing bias no longer occurs for example. Nevertheless, these systems too still require complex sample preparation.

SUMMARY

Against this background, the approach presented here presents a sequencing device for reproducing and separating molecular chains, additionally a method for separating molecular chains obtained from an amplification reaction, and a method for producing such a sequencing device, a device for controlling such methods and lastly a corresponding computer program. Advantageous developments of and improvements to the device are possible by the measures described below.

What is presented is a microfluidic sequencing device for reproducing and separating molecular chains. The sequencing device is designed to accommodate biochemical material. The sequencing device comprises at least one supply opening for supplying biochemical material into the sequencing device. Furthermore, the sequencing device comprises at least one microfluidic separation-procedure unit comprising a separation-procedure channel, the separation-procedure channel comprising at least one amplification cavity for reproducing molecular chains supplied via the supply opening, as biochemical material, and at least one separation unit microfluidically connectable or connected to the amplification cavity and comprising a multipore material, the separation unit being designed to separate nucleic acids from further macromolecular constituents and/or to resolve nucleic acids. In addition, the sequencing device comprises a discharge opening for discharging nucleic acids resolved in the separation-procedure unit, as biochemical material, from the sequencing device.

The approach presented here offers the advantages that the risk of a DNA contamination drops as a result of the integration of the amplification reaction in the sequencing device and/or the method, since the products of the amplification reaction need not be manually pipetted before sequencing. The separation unit composed of multipore material offers the advantage that the risk of clogging of the pores with constituents of the amplification reaction decreases owing to the many entry points of the porous material.

A sequencing device for reproducing and separating molecular chains can be understood to mean an integrated device in which both an amplification reaction, and the separation of the at least one molecular chain from the amplification reaction, can take place. The sequences resulting after separation can be evaluated using a conventional evaluation unit. The amplification reaction can, for example, be a polymerase chain reaction (PCR), especially a PCR in which the resultant product strand is terminated by the use of a chain-termination nucleotide (dideoxyribonucleoside triphosphate). The molecular chains to be reproduced and separated can, for example, be deoxyribonucleic acid molecular chains (DNA) or be ribonucleic acid molecular chains (RNA) or be fragments of these molecular chains. Thus, the sequencing device can, for example, be used to sequence a DNA sample by reproducing the DNA of the sample, generating chain-termination products by means of chain-termination nucleotides, and separating macromolecular constituents from the chain-termination products and/or resolving the chain-termination products, i.e., the DNA sequences, in the separation unit. The length of the DNA sequences can then be measured.

The biochemical material can, for example, be DNA or RNA or be a fragment of these two acids, or be polymerase or be a reaction component, such as, for example, a primer for the amplification of a particular DNA sequence, or be a modified or artificial DNA nucleotide and/or a chain-termination nucleotide.

According to one embodiment, the sequencing device can, for example, be a microfluidic lab-on-a-chip and/or a system-on-a-chip, or be a building block of a microfluidic lab-on-a-chip and/or a system-on-a-chip. Owing to its size, such a sequencing building block can be used as a miniaturized stand-alone sequencer or else as a building block in a lab-on-a-chip. In the case of the latter, a sample-to-sequence functionality is then realizable. This is, for example, of interest in the area of oncology, since a wide variety of mutations are present on various oncogenes such as, for example, EGFR, KRAS, NRAS and BRAF, which mutations can be queried in a simple manner by means of the sequencing device, for example in a therapeutic monitoring setting at the point of care.

According to one embodiment, the separation unit can comprise porous silicon at least in part and/or polycarbonate filter membranes at least in part, for example track-etched membranes, and/or fabric-type polymer membranes at least in part and/or nanoporous metal oxide at least in part, for example aluminum oxide. Additionally or alternatively, the separation unit can comprise an array of microposts at least in part, for example realized in silicon, silicon oxide, silicon nitrite or photoresist, the intervals between the posts being between 1 and 1000 nm, preferably between 50 and 300 nm. Further additionally or alternatively, the separation unit can comprise an acrylamide gel at least in part and/or an agarose gel at least in part; for this purpose, the separation unit is then formed as a microfluidic channel in which a gel is introduced and polymerized to completion. The porous character increases the residence time of the biochemical material in the separation unit, and this improves the differentiability of chain-termination products, for example DNA fragments of different length. The pores can, for example, be produced by means of focused ion beam or the transfer of a graphene membrane into a cavity.

The separation unit can be formed in the manner of a path; hereinafter, the separation unit is also called a separation path. The separation path can, as described, be preferably a porous solid phase, a microtechnologically produced column array or else a classic sequencing gel. The use of a multipore porous material for the separation unit offers various advantages over the use of a 2.5D pore. A 2.5D pore is a straight pore in a thin (graphene) layer: the production of the separation unit as a separation path composed of a porous material can advantageously be simpler than the production of, for example, a graphene layer which must contain pores having diameters of approx. 1-3 nm in a controllable number. A separation path, for example composed of porous silicon, can be produced using common methods, as exist in wafer fabrication.

The separation path for the resolving of molecular chains, for example DNA molecules, can be lengthened by the fabric-type formation of the porous material. As a result, the resolution capacity for nucleobases can be improved, since the individual fragments can be separated better from one another owing to the longer separation path. If, for example, electric fields are used to move the molecular chains through the separation unit according to one embodiment, the electric fields can be advantageously smaller than in the case of a nanopore approach with few pores, since there are more entry points/threading points into the multipore separation path for the molecular chains, for example the DNA fragments. As a result, the migration rate decreases, and this brings an improvement with respect to resolution (sampling rate), this advantageously facilitating measurement of the separation products, for example the DNA sequences.

Depending on the embodiment, it is possible for very many DNA fragments to migrate through the separation path at the same time because the porous material adjacent to an amplification cavity comprises more entry points than individual 2.5D pores, and this results in a stronger change in an electric measurement signal or, for example, provides easily detectable optical signals in the case of stained DNA.

According to one embodiment, the separation unit can comprise at least two multipore layers of different porosity. What can be understood under the definition of porosity is a property which describes a number of pores per unit of volume. Advantageously, it is thus possible to separate nucleic acids from further macromolecular constituents, for example polymerase, and/or to resolve nucleic acids in a first layer. Through a series connection of layers of different porosity in the separation unit, it is advantageously possible to, for example, perform various separation steps and/or separation processes. For example, what can be achieved is that macromolecular constituents (e.g., polymerase) can be removed in a first layer having a pore diameter D1, whereas the nucleic acids (DNA fragments) can be resolved in a second layer having a pore diameter D2, with D1 being greater than D2. Expressed in other words, what can be advantageously realized with the same process technology is a cleanup of the product of the amplification reaction, for example of the PCR product, before the actual sequencing. The background thereto can be seen in the cleanup of the PCR product before capillary electrophoresis in Sanger sequencing. This function can be assumed by a separation unit comprising multiple multipore layers of different porosity.

According to one embodiment, the separation unit can have a width which substantially corresponds to the width of the amplification cavity. For example, the width of the amplification cavity can exactly correspond to the width of the separation unit, or there can be a slight deviation of the width of the separation unit, for example in the range from 5% to 10% of the width of the separation unit. This advantageously allows a particularly simple production of the separation-procedure unit, in which the amplification cavity and the separation unit can be arranged in a separation-procedure channel, since the separation-procedure unit can have an opening of constant width for the at least one separation-procedure channel. The width of the separation unit can correspond to between 0.1% and 100% of the width of the amplification cavity, preferably between 50% and 100%.

According to one embodiment, the amplification cavity can be connectable or connected to the separation unit by a wall having a bottleneck. This has the advantage that the amount of the biochemical material, for example DNA, present in the separation unit during the separation process is limited, and this advantageously allows a more accurate measurement, since only a limited amount of biochemical material, particularly of the chain-termination products, are situated in the separation unit at the same time. Mixed signals due to too many and/or overlapping chain-termination products of different length in the separation unit can be avoided as a result.

According to one embodiment, the supply opening and/or the discharge opening can be formed as a constriction of the separation-procedure channel. The supply opening can be a constriction in the amplification cavity and/or the discharge opening can be a constriction of the separation unit. This integrated arrangement of the supply opening and the discharge opening on the separation-procedure channel advantageously lowers the risk of a contamination, since it is thus possible for biochemical material to be directly introduced into the sequencing device and discharged therefrom.

According to one embodiment, the sequencing device can also comprise a field-development unit for generating an electric field across the separation unit in order to convey a molecular chain through the separation path by electrophoresis. This advantageously allows an electrophoretic separation of the molecular chains in the porous separation unit. In addition, a measurement of the migration rate of the chain-termination products, for example DNA sequences of the terminated PCR product strands, can be used to determine the length of the chain-termination products.

The device comprising the "field-development unit for generating an electric field" can moreover be used for the development/application of a dielectrophoretic separation principle in order, for example, to separate constituents of the PCR reaction from one another by dielectrophoresis. This means that it is, for example, possible to separate polymerase from the termination products in order to minimize the risk of clogging of pores by macromolecular constituents such as, for example, polymerase.

According to one embodiment, at least one reaction component and at least one artificial DNA nucleotide and/or one chain-termination nucleotide can be kept in reserve in the amplification cavity of the sequencing device. Additionally or alternatively, the amplification cavity can be designed to accommodate a liquid for an amplification reaction. The reaction component kept in reserve can, for example, be a primer, for example in the form of a sequence of nucleotides for the amplification of a particular molecular chain, for example a particular DNA sequence. The artificial DNA nucleotide can, for example, be a modified nucleotide, and the chain-termination nucleotide can, for example, be a so-called stop nucleotide, a ddNTP (dideoxyribonucleoside triphosphate) comprising one of the nucleobases thymine, guanine, adenine or cytosine. The chain-termination nucleotides can, for example, also additionally be labeled with fluorophores, radioactively or redox-actively.

According to one embodiment, the separation-procedure unit can comprise at least two amplification cavities, especially four amplification cavities, which are designed to contain at least one identical reaction component each and at least one different, artificial DNA nucleotide each and/or at least one respectively different chain-termination nucleotide and/or are designed to accommodate a liquid for an amplification reaction. The respectively different chain-termination nucleotide can, for example, be an above-described stop nucleotide comprising a respectively different nucleobase, namely thymine, guanine, adenine or cytosine, the result being that each of the four amplification cavities after the reaction can contain a chain-termination nucleotide terminated with a respectively different nucleobase. The liquid for an amplification reaction can, for example, be a commercially available amplification mix. The amplification mix can, for example, also contain an intercalating dye in order to stain the resultant amplification product. Additionally or alternatively, the liquid for the amplification reaction can contain molecular chains, especially sample DNA, to be sequenced.

What is furthermore advantageous is one embodiment of the approach presented here, in which the sequencing device comprises a length-determination unit for determining a length of resolved nucleic acids as biochemical material. In this way, the biochemical material can be analyzed for the presence of particular properties in a very rapid and efficient manner.

Furthermore, what is presented is a method for separating molecular chains obtained from an amplification reaction, using one embodiment of the presented sequencing device, it being possible for the method to comprise at least the following steps:
  introducing a liquid for an amplification reaction into the at least one amplification cavity in order to prepare for an amplification reaction;
  conducting a sealing liquid across the supply opening and the discharge opening in order to seal the supply opening and the discharge opening;
  performing an amplification reaction in order to generate at least one molecular chain and terminating obtained molecular chains in order to generate chain-termination products; and
  applying a voltage between the supply region and the discharge region in order to fill the at least one separation unit and separating the at least one molecular chain generated in the separation unit in order to obtain chain-termination products.

In the introduction step, the liquid for the amplification reaction that can be introduced is such a liquid, as described above, comprising at least one molecular chain to be sequenced, for example sample DNA, for the generation of chain-termination products from the amplification reaction.

In the step of conducting a sealing liquid across the supply opening and the discharge opening, the sealing liquid that can be used is, for example, an oil, especially a mineral oil, a paraffin oil, fluorinated oil or silicone oil, in order to seal the supply opening and the discharge opening, this advantageously lowering the risk of a contamination.

In the step of performing an amplification reaction, what can be performed is, for example, a polymerase chain reaction (PCR), which can, for example, comprise up to 80 cycles, preferably between 5 and 40 cycles. Molecular chains can be generated in the amplification reaction. The generated molecular chains can, for example, be terminated by modified nucleotides or chain-termination nucleotides, with the result that chain-termination products of different length can arise, depending on when a modified nucleotide or a chain-termination nucleotide is incorporated. Said chain-termination products can, for example, be fragments of the DNA to be sequenced, i.e., DNA sequences.

In the step of applying a voltage between the supply region and the discharge region in order to fill the at least one separation unit, it is, for example, possible to apply an electric field across the separation unit using a field-development unit in order to fill the at least one separation unit. Owing to the electrophoretic migration of the products of the amplification reaction through the separation unit, it is possible to separate the products of the amplification reaction, and the chain-termination products can be obtained as a result. This linking of the amplification reaction with the separation process advantageously lowers the risk of a DNA contamination, since the products of the amplification reaction need not be manually pipetted before sequencing. Additionally or alternatively, it is also possible to apply a pressure difference in the separation-procedure unit for the filling of the separation unit, i.e., for fluidic actuation.

Additionally or alternatively, it is also possible to utilize capillary forces, for example for wetting of the separation unit.

Furthermore, what is presented is a method for detecting chain-termination products, the method comprising at least the steps of the above-presented method and a step for measuring the length of the chain-termination products in order to detect the of the sequence of the chain-termination products. The step of measuring the length of the chain-termination products in order to detect the sequence of the chain-termination products can, for example, be effected in the form of an optical reading or a current measurement. In the case of a large-area contact, for example in the case of three or more pores at the entry point from the amplification cavity into the porous separation unit, it is possible for resolved and stained product fragments of the amplification reaction to be preferably read optically. Alternatively, it is, for example, possible to measure the passage time of the product fragments of the amplification reaction through the separation unit via a current measurement at known (pre-calibrated) migration rate. If the contact region between the separation unit and the amplification cavity is reduced, for example in the case of fewer than three pores at the entry point from the amplification cavity into the porous separation unit, it is preferably possible to measure the duration of the change in current flow during passage of individual product fragments.

The presented methods and the presented device can, for example, use the established sequencing method by Frederick Sanger and be integrated and miniaturized by means of microsystem technology (MEMS technology) and silicon.

Such a device comprises at least one amplification region in the form of an amplification cavity that is connected to a miniaturized separation unit, for example in the form of a separation path. In said separation path, it is possible to resolve the amplification products generated in the amplification region, which amplification products are of different length in accordance with the Sanger method.

Furthermore, what is presented is a method for producing one embodiment of the presented sequencing device, the method comprising at least the following steps:

forming a separation unit composed of a multipore material; and connecting the separation unit to an amplification cavity in a separation-procedure unit in order to produce the sequencing device.

In the step of forming the separation unit composed of multipore material, it is possible to use a coating method, for example a chemical vapor deposition (LPCVD). Additionally or alternatively, the separation unit can, for example, be hydrophilized or hydrophobized by means of vapor-coating, sputtering or silanization. According to one embodiment, the separation unit can, for example, also be produced from porous silicon using a common method, such as in the case of wafer fabrication. The production of the separation path from a porous material is advantageously simple to implement.

In the step of connecting the separation unit to an amplification cavity in a separation-procedure unit in order to produce the sequencing device, the multipore separation unit can be microfluidically connected to an amplification cavity in a separation-procedure channel. The direct connection of the separation unit to an amplification cavity advantageously allows a particularly compact construction of the sequencing device.

Said method can, for example, be implemented in software or hardware or in a mixed software-and-hardware form, for example in a controller.

The approach presented here further provides a device which is designed to perform, control or implement the steps of a variant of a method presented here in corresponding apparatuses. This variant of the disclosure in the form of a device can, too, achieve the object underlying the disclosure in a rapid and efficient manner. The device can, for example, comprise a formation unit for forming the separation unit composed of multipore material and a connection unit for connecting the separation unit to an amplification cavity in a separation-procedure unit.

Here, a device can be understood to mean an electrical instrument which processes sensor signals and outputs control and/or data signals depending thereon. The device can comprise an interface, which can be of a hardware and/or software design. In the case of a hardware design, the interfaces can, for example, be part of a so-called system ASIC which contains a wide variety of functions of the device. However, it is also possible that the interfaces are separate, integrated circuits or consist of discrete components at least in part. In the case of a software design, the interfaces can be software modules, which, for example, are present on a microcontroller in addition to other software modules.

The approach presented here further provides a controller which is designed to perform, control or implement the steps of a variant of a method presented here in corresponding apparatuses. These variants of the disclosure in the form of a controller can, too, achieve the object underlying the disclosure in a rapid and efficient manner.

Also advantageous is a computer program product or computer program containing program code that can be stored on a machine-readable carrier or storage medium such as a semiconductor memory, a hard drive storage device or an optical storage medium and is used for performing, implementing and/or controlling the steps of the method according to any of the above-described embodiments, especially when the program product or program is executed on a computer or a device.

BRIEF DESCRIPTION OF THE DRAWING

Exemplary embodiments of the approach presented here are depicted in the drawings and more particularly elucidated in the following description, where.

DETAILED DESCRIPTION

In the following description of favorable exemplary embodiments of the present disclosure, identical or similar reference signs are used for the elements which are depicted in the various figures and act in a similar manner, in order to dispense with a repeated description of said elements.

Figure 1A:
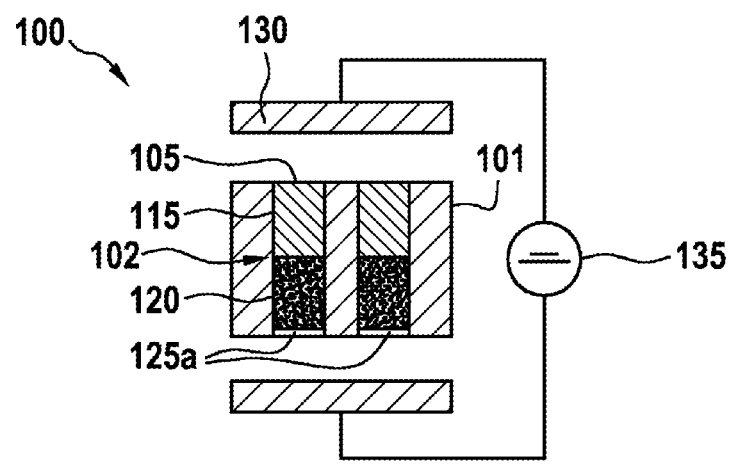
FIGS. 1A to 1C show a schematic representation of a sequencing device according to various exemplary embodiments.

FIG. 1A shows a schematic representation of a cross-section of a microfluidic sequencing device 100 according to one exemplary embodiment. The sequencing device 100 is designed to accommodate biochemical material and to reproduce and separate molecular chains. The sequencing device 100 comprises at least one separation-procedure unit 101. The separation-procedure unit 101 comprises at least one separation-procedure channel 102. By way of example, this exemplary embodiment shows two such separation-procedure channels 102. The separation-procedure unit 101 comprises at least one supply opening 105, at least one microfluidic separation-procedure channel 102 comprising an amplification cavity 115 and a separation unit 120, and one discharge opening 125. The supply opening 105 is designed to supply biochemical material into the sequencing device 100. The at least one separation-procedure channel 102 is designed to microfluidically connect the amplification cavity 115 to the separation unit 120. The amplification cavity 115 is designed to reproduce molecular chains. The separation unit 120 consists of multipore material and is designed to separate nucleic acids from further macromolecular constituents and/or to resolve nucleic acids. The discharge opening 125 is designed to discharge biochemical material from the sequencing device 100.

According to one exemplary embodiment, biochemical material, especially a liquid for an amplification reaction, can be introduced into the amplification cavity 115 via the supply opening 105. Connected to the amplification cavity 115 is the separation unit 120, which opens into the discharge opening 125. Moreover, the separation-procedure unit 101 is, according to one exemplary embodiment, formed to be electrically contactable with a voltage source 135 at the supply opening 105 and at the discharge opening 125 via a field-development unit 130 in order to convey PCR products through the separation path by electrophoresis. Here, the field-development unit 130 can use either direct voltage or alternatively alternating voltage.

According to one exemplary embodiment, the separation unit 120 comprises porous silicon at least in part and/or polycarbonate filter membranes at least in part, especially track-etched membranes. Additionally or alternatively, the separation unit 120 comprises fabric-type polymer membranes at least in part and/or nanoporous metal oxide at least in part and/or an array of microposts at least in part and/or an acrylamide gel at least in part and/or an agarose gel at least in part. The porous character of the separation unit 120 increases the residence time in the separation unit 120, and this improves the differentiability of DNA fragments of different length.

According to one exemplary embodiment, the separation unit 120 has a width which substantially corresponds to the width of the amplification cavity 115.

According to one exemplary embodiment, the supply opening 105 is arranged at the entrance of the amplification cavity 115, in the flow direction of supplying biochemical material, especially the liquid for the amplification reaction. According to said exemplary embodiment, the discharge opening 125 is substantially formed in the width of the separation unit 120, at the exit of the separation unit 120, from which the biochemical material, especially the separated chain-termination products, is discharged.

Figure 1B:
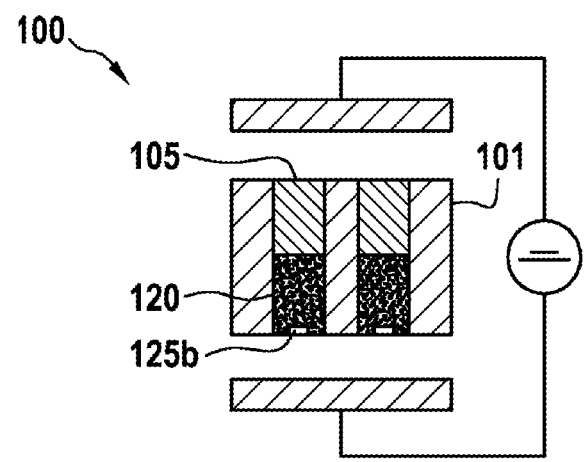

FIG. 1B shows a schematic representation of a cross-section of a microfluidic sequencing device 100 according to a further exemplary embodiment. Said exemplary embodiment differs from the preceding one only in the formation of the discharge opening. In said exemplary embodiment, the discharge opening 125*b* is formed as a constriction at the exit of the separation unit 120.

Figure 1C:
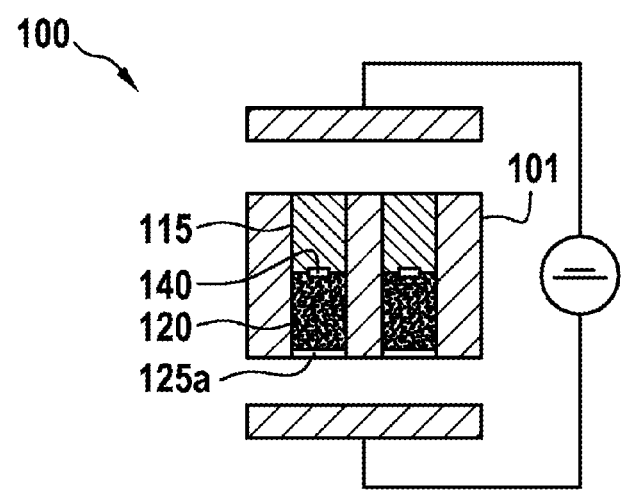

FIG. 1C shows a schematic representation of a cross-section of a microfluidic sequencing device 100 according to a further exemplary embodiment. Said exemplary embodiment differs from the two preceding ones only by a bottleneck 140 between the amplification cavity 115 and the separation unit 120. The discharge opening 125*a* corresponds to the formation depicted in FIG. 1A. According to one exemplary embodiment, the amplification cavity 115 is connectable or connected to the separation unit 120 by a wall having a bottleneck 140.

The amount of the biochemical material, especially an amount of DNA, present in the separation unit 120 during the separation process is limited so as to minimize mixed signals (when too many DNA fragments of different length are situated and/or overlap in the separation region) in a measurement.

Figure 2:
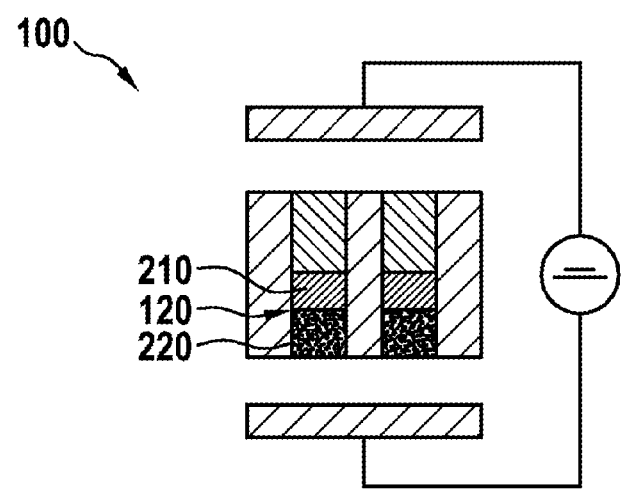
FIG. 2 shows a schematic representation of a sequencing device according to a further exemplary embodiment.

FIG. 2 shows a schematic representation of a sequencing device 100 according to a further exemplary embodiment. Said exemplary embodiment differs from the preceding ones only by the formation of the separation unit 120. According to said exemplary embodiment, the separation unit 120 comprises at least two multipore layers 210, 220 of different porosity. By way of example, this representation shows a first multipore layer 210 and a second multipore layer 220, which have differing porosity. The series connection of layers 210, 220 of different porosity especially allows various separation steps, for example that macromolecular constituents are removed in a first layer 210, whereas the chain-termination products, especially nucleic acids (DNA fragments), are resolved in a second layer 220.

Figure 3:
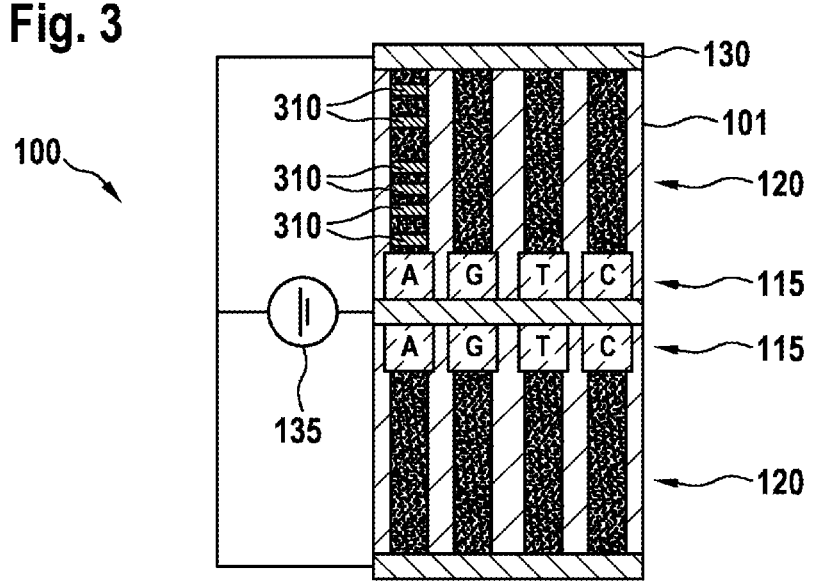
FIG. 3 shows a schematic representation of a sequencing device according to a further exemplary embodiment.

FIG. 3 shows a schematic representation of a sequencing device 100 according to a further exemplary embodiment. Said exemplary embodiment differs from the preceding ones only by the content of the amplification cavity 115 and by the number of the depicted separation-procedure channels in the separation-procedure channel apparatus 101. Moreover, the separation-procedure channel apparatus 101 consists here, by way of example, of two segments, which each comprise four separation-procedure channels 102 comprising the amplification cavity 115 and the separation unit 120, the segments of the separation-procedure channel apparatus 101 being shown here as counter-images (in a mirrored manner).

According to this exemplary embodiment, at least one reaction component and at least one artificial DNA nucleotide and/or one chain-termination nucleotide of the bases A, G, T, C is kept in reserve in each amplification cavity 115. Additionally or alternatively, the amplification cavity 115 is designed to accommodate a liquid for an amplification reaction.

According to one exemplary embodiment, the separation-procedure unit 101 comprises at least two amplification cavities 115, especially four amplification cavities 115. By way of example, what are shown per segment of the separation-procedure unit 101 are four amplification cavities 115 each. The amplification cavities 115 are designed to contain at least one identical reaction component each and at least one different, artificial DNA nucleotide each and/or at least one respectively different chain-termination nucleotide A, G, T, C. Additionally or alternatively, the amplification cavity 115 is designed to accommodate a liquid for an amplification reaction.

According to the exemplary embodiment shown here, two different DNA sequences can be sequenced in the sequencing device 100, especially one in each segment of the separation-procedure unit 101. To this end, the four amplification cavities 115 in each of the two segments of the separation-procedure unit 101 comprise one separation cavity 115 for the generation of each of the differently terminated chain-termination products 310 (especially terminated with A=adenine, G=guanine, T=thymine, C=cytosine). Each of the amplification cavities 115 is connected to one separation unit 120. By means of a field-development apparatus 130 and a voltage source 135, it is possible to generate an electric field across the separation units 120. In one operation, a dye is supplied to the liquid for the amplification reaction before or after the reaction, which dye allows a fluorometric detection of chain-termination products 310 obtained in the amplification reaction and resolved by the separation unit 120. It is thus possible to differentiate various chain-termination products 310 in a separation unit 120 in terms of their length.

Figure 4:
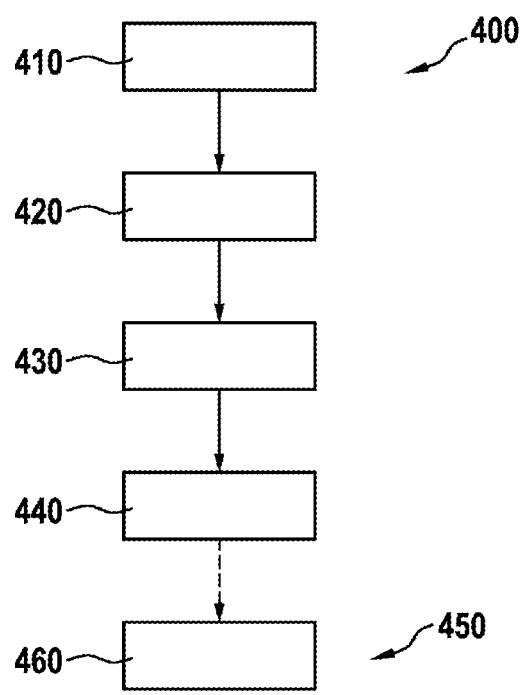
FIG. 4 shows a flow chart of a method for reproducing and separating molecular chains according to one exemplary embodiment.

FIG. 4 shows a flow chart of a method 400 for separating molecular chains obtained from an amplification reaction, according to one exemplary embodiment. The method 400 is executable using an already described microfluidic sequencing device 100 according to one of the exemplary embodiments, the method 400 comprising at least one introduction step 410, one conduction step 420, one performance step 430 and one application step 440.

In the introduction step 410, a liquid for an amplification reaction is introduced into the at least one amplification cavity in order to prepare for an amplification reaction. For example, a pressure difference is applied between the entrance of the amplification cavity and the exit of the separation unit for the introduction step in order to introduce the liquid for an amplification reaction into the separation-procedure channel. It is equally possible to utilize capillary forces for fluidic actuation, i.e., for the introduction of the liquid for an amplification reaction.

In the conduction step 420, a sealing liquid is conducted across the supply opening and the discharge opening in order to seal the supply opening and the discharge opening. In this connection, the discharge opening and the supply opening are flushed with a sealing liquid.

In the performance step 430, the conditions for an amplification reaction are provided and an amplification reaction is performed in order to generate at least one molecular chain. At the same time, the molecular chains obtained in the amplification reaction are terminated in order to generate chain-termination products. Termination is achieved by an artificial DNA nucleotide and/or a chain-termination nucleotide.

In the application step 440, a voltage is applied between the supply region and the discharge region in order to fill the at least one separation unit. Moreover, the at least one molecular chain generated is resolved in the separation unit in order to obtain chain-termination products. In addition, a running buffer can be admitted to the separation unit at its ends before the application of voltage. As a result, capillary filling of the separation unit occurs, and this improves the migration behavior of the chain-termination products upon application of an electric field.

In addition, FIG. 4 shows a flow chart of a method 450 for detecting chain-termination products. The method 450 comprises at least the steps of the method 400, namely an introduction step 410, a conduction step 420, a performance step 430 and an application step 440, and additionally a measurement step 460, which can take place at the same time as the application step 440.

In the measurement step 460, the length of the chain-termination products is measured in order to detect the sequence of the chain-termination products. For example, what is measured at the same time as the application step 440 is the current at the separation-procedure unit that is dependent on the amount of the chain-termination products and/or what is measured is the rate of passage of individual fragments of biochemical material. Additionally or alternatively, the resolved and previously stained chain-termination products are read optically.

Figure 5:
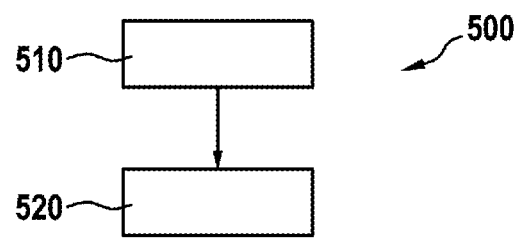
FIG. 5 shows a flow chart of a method for producing a sequencing device according to one exemplary embodiment.

FIG. 5 shows a flow chart of a method 500 for producing a sequencing device according to one presented exemplary embodiment. The method 500 comprises at least one formation step 510 and one connection step 520.

In the formation step 510, a separation unit composed of a multipore material is formed. The multipore separation unit can be formed by means of a coating method, especially a chemical vapor deposition (LPCVD). Additionally or alternatively, the separation unit can also be produced from porous silicon using a common method, such as in the case of wafer fabrication, and/or be hydrophilized or hydrophobized by means of vapor-coating, sputtering or silanization.

In the connection step, the separation unit is connected to an amplification cavity in a separation-procedure unit in order to produce the sequencing device.

Figure 6:
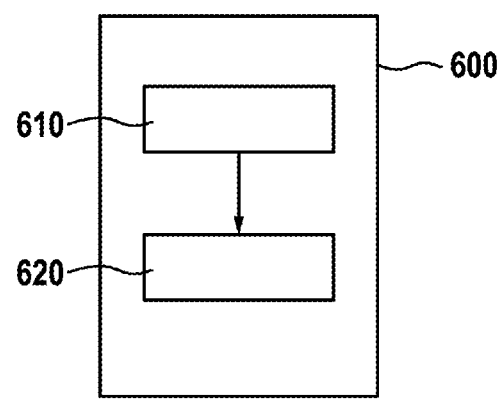
FIG. 6 shows a schematic representation of a device for executing or controlling the steps of a method for producing a sequencing device according to one exemplary embodiment.

FIG. 6 shows a schematic representation of a device 600 for executing and/or controlling the steps of a method for producing a sequencing device according to one exemplary embodiment.

The device 600 is configured to execute and/or control the steps of the method in corresponding units. The device comprises at least one formation unit 610 and one connection unit 620. The formation unit is designed to control and/or execute the step of forming a separation unit composed of multipore material and the connection unit 620 is designed to execute and/or control the step of connecting the separation unit to an amplification cavity in a separation-procedure unit.

Figure 7:
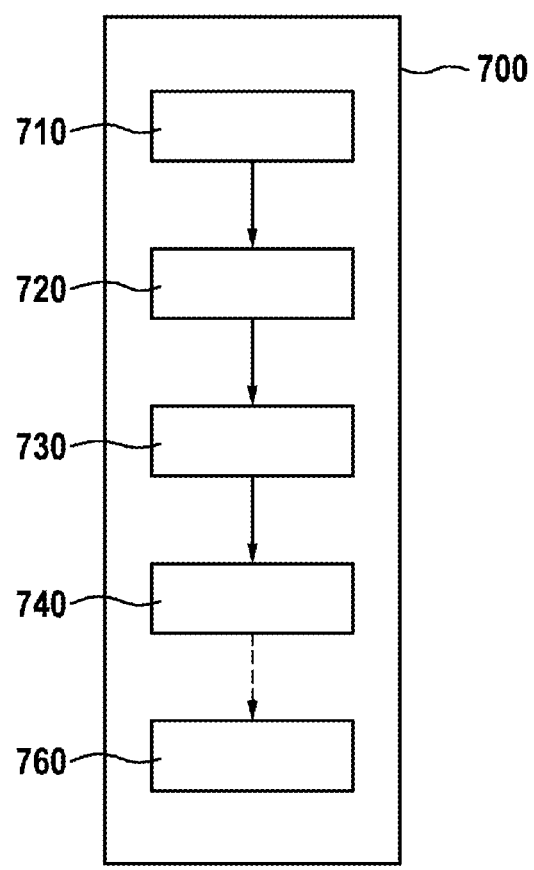
FIG. 7 shows a schematic representation of a device for executing or controlling the steps of a method for reproducing and separating molecular chains according to one exemplary embodiment.

FIG. 7 shows a schematic representation of a device 700 for executing and/or controlling the steps of a method 400 for reproducing and separating molecular chains and/or of a method 450 for detecting chain-termination products according to one exemplary embodiment. The device 700 is configured to execute and/or control the steps of the method in corresponding units. The device comprises at least one introduction unit 710, one conduction unit 720, one performance unit 730 and one application unit 740. The introduction unit is designed to introduce a liquid for an amplification reaction into the at least one amplification cavity in order to prepare for an amplification reaction. The conduction unit is designed to conduct a sealing liquid across the supply opening and the discharge opening in order to seal the supply opening and the discharge opening. The performance unit is designed to perform an amplification reaction in order to generate at least one molecular chain and to terminate the at least one molecular chain obtained in order to generate chain-termination products. The application unit is designed to apply a voltage between the supply opening and the discharge opening in order to fill the at least one separation unit and in order to separate the at least one molecular chain generated in the separation unit in order to obtain chain-termination products.

In addition, the device 700 can comprise a measurement unit which is designed to measure the length of the chain-termination products in order to detect the sequence of the chain-termination products.

If an exemplary embodiment comprises an "and/or" link between a first feature and a second feature, this is to be interpreted as meaning that the exemplary embodiment comprises both the first feature and the second feature according to one embodiment and either only the first feature or only the second feature according to a further embodiment.

The invention claimed is:

1. A microfluidic sequencing device for reproducing and separating molecular chains, the sequencing device configured to accommodate biochemical material, the sequencing device comprising:
   a supply opening configured for supplying biochemical material into the sequencing device;
   at least one microfluidic separation-procedure unit comprising at least one separation-procedure channel comprising (i) at least one amplification cavity configured to reproduce molecular chains supplied via the supply opening as biochemical material, and (ii) at least one separation unit microfluidically connectable or connected to the at least one amplification cavity and including a multipore material, the at least one separation unit configured to separate nucleic acids from further macromolecular constituents and/or to resolve nucleic acids; and a discharge opening configured for discharging nucleic acids resolved in the at least one separation-procedure unit from the sequencing device as biochemical material, wherein the at least one separation unit comprises at least one of the following: porous silicon, polycarbonate filter membranes, fabric-type polymer membranes, nanoporous metal oxide, and an array of microposts.

2. The sequencing device as claimed in claim 1, wherein the at least one separation unit comprises at least two multipore layers of different porosity.

3. The sequencing device as claimed in claim 1, wherein the at least one separation unit has a width which substantially corresponds to a width of the at least one amplification cavity.

4. The sequencing device as claimed in claim 1, wherein the at least one amplification cavity is connectable or connected to the at least one separation unit by a wall having a bottleneck.

5. The sequencing device as claimed in claim 1, wherein the supply opening and/or the discharge opening is formed as a constriction of the at least one separation-procedure channel.

6. The sequencing device as claimed in claim 1, further comprising:
a field-development unit configured to generate an electric field across the at least one separation unit in order to convey a molecular chain through the at least one separation unit by electrophoresis.

7. The sequencing device as claimed in claim 1, wherein:
at least one reaction component and at least one artificial DNA nucleotide and/or one chain-termination nucleotide is kept in reserve in the at least one amplification cavity; and/or
the at least one amplification cavity is configured to accommodate a liquid for an amplification reaction.

8. The sequencing device as claimed in claim 1, wherein:
the at least one amplification cavity of the at least one separation-procedure unit comprises at least two amplification cavities, and
each of the at least two amplification cavities contains (a) at least one identical reaction component and (b) at least one different, artificial DNA nucleotide and/or at least one respectively different chain-termination nucleotide; and/or
each of the at least two amplification cavities contains is designed to accommodate a liquid for an amplification reaction.

9. The sequencing device as claimed in claim 1, further comprising:
a length-determination unit configured to determine a length of resolved nucleic acids as biochemical material.

10. A method for separating molecular chains obtained from an amplification reaction, using a microfluidic sequencing device that has (a) a supply opening configured for supplying biochemical material into the sequencing device; (b) at least one microfluidic separation-procedure unit including at least one separation-procedure channel that includes (i) at least one amplification cavity configured to reproduce molecular chains supplied via the supply opening as biochemical material, and (ii) at least one separation unit microfluidically connectable or connected to the at least one amplification cavity and including a multipore material, the at least one separation unit configured to separate nucleic acids from further macromolecular constituents and/or to resolve nucleic acids; and a discharge opening configured for discharging nucleic acids resolved in the at least one separation-procedure unit from the sequencing device as biochemical material, the method comprising:
introducing a liquid for the amplification reaction into at least one amplification cavity of at least one separation-procedure channel of at least one microfluidic separation-procedure unit in order to prepare for an amplification reaction;
conducting a sealing liquid across the supply opening and the discharge opening in order to seal the supply opening and the discharge opening;
performing the amplification reaction in order to generate at least one molecular chain and terminating obtained molecular chains in order to generate chain-termination products; and
applying a voltage between the supply opening and the discharge opening in order to fill the at least one separation unit and separating the at least one molecular chain generated in the separation unit in order to obtain chain-termination products.

11. The method as claimed in claim 10, further comprising:
measuring a length of the chain-termination products in order to detect a sequence of the chain-termination products.

12. A device which is configured to execute and/or control the steps of the method as claimed in claim 10 in corresponding units.

13. A computer program which is configured to execute and/or control a microfluidic sequencing device, which has (a) a supply opening configured for supplying biochemical material into the sequencing device; (b) at least one microfluidic separation-procedure unit including at least one separation-procedure channel that includes (i) at least one amplification cavity configured to reproduce molecular chains supplied via the supply opening as biochemical material, and (ii) at least one separation unit microfluidically connectable or connected to the at least one amplification cavity and including a multipore material, the at least one separation unit configured to separate nucleic acids from further macromolecular constituents and/or to resolve nucleic acids; and a discharge opening configured for discharging nucleic acids resolved in the at least one separation-procedure unit from the sequencing device as biochemical material, so as to execute program instructions stored in memory to operate the microfluidic sequencing device to separate molecular chains obtained from an amplification reaction by:
introducing a liquid for an amplification reaction into at least one amplification cavity of at least one separation-procedure channel of at least one microfluidic separation-procedure unit in order to prepare for an amplification reaction;
conducting a sealing liquid across the supply opening and the discharge opening in order to seal the supply opening and the discharge opening;
performing an amplification reaction in order to generate at least one molecular chain and terminating obtained molecular chains in order to generate chain-termination products; and
applying a voltage between the supply opening and the discharge opening in order to fill the at least one separation unit and separating the at least one molecular chain generated in the separation unit in order to obtain chain-termination products.

14. The method as claimed in claim 13, wherein the computer program is stored on a machine-readable storage medium.

15. The sequencing device as claimed in claim 1, wherein the polycarbonate filter membranes are track-etched membranes.

16. The sequencing device as claimed in claim 8, wherein the at least two amplification cavities includes at least four amplification cavities.

* * * * *